United States Patent [19]
Goto et al.

[11] Patent Number: 5,210,299
[45] Date of Patent: May 11, 1993

[54] METHOD FOR PRODUCTION OF N-(2-CHLOROETHYL) METHANESULFONAMIDE

[75] Inventors: Yujiro Goto, Kawasaki; Mitsuaki Yagisawa, Yokohama; Masao Kitano, Kamakura, all of Japan

[73] Assignee: Nippon Shokubai Co., Ltd., Osaka, Japan

[21] Appl. No.: 833,087

[22] Filed: Feb. 10, 1992

[30] Foreign Application Priority Data

Jul. 29, 1991 [JP] Japan .................... 3-188736

[51] Int. Cl.$^5$ .................................. C07C 303/36
[52] U.S. Cl. .................................................. 564/98
[58] Field of Search .............. 564/95, 96, 97, 98, 564/413, 487; 548/969

[56] References Cited

U.S. PATENT DOCUMENTS

| | | | |
|---|---|---|---|
| 2,288,178 | 6/1942 | Bestian | 564/98 |
| 3,179,655 | 4/1965 | Cobb | 548/969 |
| 3,336,294 | 8/1967 | Miller et al. | 548/969 |
| 3,336,383 | 8/1967 | Linden et al. | 564/98 |
| 3,956,385 | 5/1976 | Suda et al. | 260/556 A |

FOREIGN PATENT DOCUMENTS 48-85535 11/1973 Japan .
49-085022 8/1974 Japan .
1430882 4/1986 United Kingdom .

OTHER PUBLICATIONS

Chem. Abstract, vol. 80, No. 11, Mar. 1974.
Chem. Abstract, vol. 82, No. 13, Mar. 1975, Abstract No. 85439.
EPO Search Report, BE 9200147, Jul. 1992.

*Primary Examiner*—Allen J. Robinson
*Assistant Examiner*—P. O'Sullivan
*Attorney, Agent, or Firm*—Omri M. Behr; Matthew J. McDonald

[57] ABSTRACT

A method for the production of N-(2-chloroethyl) methanesulfonamide of high purity, which method comprises causing methanesulfonyl chloride to react with ethylene imine in the presence of ethylene dichloride and then distilling there resultant reaction mixture thereby separating therefrom N-(2-chloroethyl) methanesulfonamide, if necessary subjecting the resultant reaction mixture to extraction from water, separating the aqueous layer consequently formed, and subjecting the organic layer resulting from said extraction to distillation thereby separating N-(2-chloroetyl) methanesulfonamide.

14 Claims, No Drawings

METHOD FOR PRODUCTION OF N-(2-CHLOROETHYL) METHANESULFONAMIDE

BACKGROUND OF THE INVENTION

1. Field of the Invention:

This invention relates to a method for producing N-(2-chloroethyl) methanesulfonamide of high quality from ethylene imine and methanesulfonyl chloride with high productivity.

2. Description of the Prior Art:

N-(2-chloroethyl) methanesulfonamide is an important substance used mainly as an intermediate for photographic chemicals and is demanded to possess high quality.

The method for producing N-(2-chloroethyl) methanesulfonamide by the reaction of ethylene imine with methanesulfonyl chloride in the presence of an alcohol of 3 to 5 carbon atoms and/or a ketone of 3 to 10 carbon atoms is disclosed in JP-A-48-85,535.

In accordance with the method which produces N-(2-chloroethyl) methanesulfonamide by the reaction of ethylene imine with methanesulfonyl chloride in the presence of an alcohol of 3 to 8 carbon atoms and/or a ketone of 3 to 10 carbon atoms as disclosed in JP-A-48-85,535, however, since the reaction temperature must be controlled to a low temperature in the range of from 5° C. to 10° C. with a view to ensuring a high yield of reaction and preventing the product, N-(2-chloroethyl) methanesulfonamide, from coloration, the reaction velocity is low and the productivity is low.

If the reaction is carried out at a temperature exceeding 10° C. for the purpose of improving the productivity of the method, the yield of the reaction is degraded because the reaction performed in the presence of an alcohol entails a secondary reaction of methanesulfonyl chloride with the alcohol. By the same token, the purity of the produced N-(2-chloroethyl) methanesulfonamide is degraded because the reaction performed in the presence of a ketone suffers prominent coloration of the produced N-(2-chloroethyl) methanesulfonamide and entails occurrence of a peculiar by-product incapable of separation by distillation. The same problem arises when both an alcohol and a ketone are used together.

An object of this invention, therefore, is to provide a novel method for the production of N-(2-chloroethyl) methanesulfonamide.

Another object of this invention is to provide a method for the production of N-(2-chloroethyl) methanesulfonamide of high quality with high productivity by the reaction of ethylene imine with methanesulfonyl chloride at an elevated temperature.

SUMMARY OF THE INVENTION

These objects are accomplished by a method for the production of N-(2-chloroethyl) methanesulfonamide of high purity, which method comprises causing methanesulfonyl chloride to react with ethylene imine in the presence of ethylene dichloride and subjecting the resultant reaction mixture to distillation thereby separating N-(2-chloroethyl) methanesulfonamide therefrom.

These objects are further accomplished by a method for the production of N-(2-chloroethyl) methanesulfonamide of high purity, which method comprises causing methanesulfonyl chloride to react with ethylene imine in the presence of ethylene dichloride, subjecting the resultant reaction mixture to extraction from water thereby separating an aqueous layer, and then subjecting the remaining organic layer to distillation thereby separating the N-(2-chloroethyl) methanesulfone amide.

This invention has the advantage of enabling N-(2-chloroethyl) methanesulfonamide of high quality to be produced with high productivity.

The ethylene dichloride to be used in this invention has extremely low reactivity with other raw materials and, therefore, does not cause degradation of the yield of reaction even when the reaction is carried out at an elevated temperature. Thus, the reaction can be carried out at the boiling point of the reaction solution and, as a result, the reaction time can be conspicuously shortened and the productivity of the reaction can be improved as compared with the conventional low-temperature reaction.

Since the reaction of ethylene imine with methanesulfonyl chloride is an exothermic reaction and further since this reaction is carried out at the boiling point of the reaction solution while ethylene imine and methanesulfonyl chloride are simultaneously and continuously supplied to the reaction vessel, the activating energy required for the reaction is supplemented by the heat of reaction of the raw materials being continuously or intermittently supplied and the excess heat of reaction is removed by the latent heat of vaporization of ethylene dichloride. As a result, the reaction commercially brings about a conspicuous economic effect of decreasing the energy supply.

Generally in the high-temperature reaction, the main reaction which forms the desired product is liable to entail such secondary reactions of raw materials, i.e. the polymerization of ethylene imine and decomposition of methanesulfonyl chloride. In this invention, the secondary reactions can be thoroughly curbed and the main reaction can be accomplished in a high yield at elevated temperatures by simultaneously supplying ethylene imine and methanesulfonyl chloride to the reaction system continuously or intermittently thereby precluding the otherwise possible accumulation of unreacted raw materials in the reaction system and supplying ethylene imine into the reaction solution thereby preventing the ethylene imine polymerizing in the gas phase part of the reaction vessel. As a result, the N-(2-chloroethyl) methanesulfonamide desired product by the reaction can be produced with high quality.

Further, the recovery of the unaltered ethylene dichloride remaining after the reaction and the separation by distillation of the N-(2-chloroethyl) methanesulfonamide, the desired product, from the unaltered ethylene dichloride are easy because the ethylene dichloride used in this invention has a boiling point widely different from that of the N-(2-chloroethyl) methanesulfonamide.

Further, in the step of extraction, highly satisfactory surface separation occurs between water and ethylene dichloride.

EXPLANATION OF THE PREFERRED EMBODIMENT

Now, the individual steps involved in the operation of this invention will be specifically described below.

The method of this invention is characterized by charging the reaction vessel with from 50 to 1,000 parts by weight, preferably from 70 to 200 parts by weight, of ethylene dichloride based on 100 parts by weight of methanesulfonyl chloride as a raw material and then supplying simultaneously ethylene imine and methanesulfonyl chloride to the reaction vessel and effecting the reaction of the raw materials at the boiling point of the reaction solution. Since the reaction is carried out at the boiling point of the reaction solution, the ethylene dichloride in the reaction solution is expelled by vaporization. The vapor of ethylene dichloride consequently arising from the reaction solution is condensed by the condenser provided for the reaction vessel and the resultant condensate can be returned to the reaction vessel to be used in the next cycle of the reaction.

The reaction vessel is composed of a stirrer and a reaction kettle provided with a condenser. Preferably, the reaction vessel has the shell thereof lined with glass, a material which is excellent in corrosionproofness against N-(2-chloroethyl) methanesulfonamide.

Though the reaction can be carried out under normal pressure, a decreased pressure, or an increased pressure, the reaction pressure is preferable to be adjusted so that the boiling point of the reaction solution will fall in the range of from 50° C. to 150° C. Most preferably, the reaction is carried out under normal pressure. In this case, the temperature of the reaction solution is in the range of from 83° C. to 100° C.

The supply of ethylene imine and methanesulfonyl chloride can be carried out intermittently or continuously and although the duration of this supply is determined by the capacity of the reaction apparatus for the removal of the heat of reaction, the supplying time is generally 0.5 to 20 hours.

The reaction of ethylene imine with methanesulfonyl chloride is theoretically an equimolar reaction. The supplying ratio of these two reactants is preferable to be so fixed that at the end point of supply, the amount of methanesulfonyl chloride will account for a proportion in the range of from 0.9 to 1.1 mols based on 1 mol of ethylene imine. During the process of the supply of ethylene imine and methanesulfonyl chloride, however, the amounts of supply of these two reactants are preferable to be so adjusted that the number of mols of methanesulfonyl chloride will be an excess relative to the number of mols of ethylene imine. Preferably, in this invention, the supply of methanesulfonyl chloride is made in an amount in the range of from 2 to 20% by weight, based on the total amount of methanesulfonyl chloride to be supplied in advance of the supply of ethylene imine and, after the start of this supply of ethylene imine, the amounts of supply of ethylene imine and methanesulfonyl chloride are adjusted so that the amount of methanesulfonyl chloride supplied preliminarily will be maintained in the reaction solution. At the end point of supply, the amount of methanesulfonyl chloride may be in the range of from 0.9 to 1.1 mols per mol of ethylene imine as previously described.

Further, for the sake of the reaction of this invention, during the supply of ethylene imine and methanesulfonyl chloride, it is preferable to supply the ethylene imine into the reaction solution as by the use of a charging tube. After the completion of the reaction, ethylene dichloride in the reaction solution is separated and recovered by distillation, and may be used in the next step as it is or, if necessary, after subjecting further purification.

From the reaction solution remaining after the recovery of ethylene dichloride, N-(2-chloroethyl) methanesulfonamide, i.e. the product aimed at can be obtained by subjecting the reaction solution to vacuum distillation. This distillation is carried out at a degree of vacuum in the range of from 0.1 to 10 torrs at a distillation temperature in the range of from 100° to 200° C.

The separation of ethylene dichloride and the more volatile component and the acquisition of N-(2-chloroethyl) methanesulfonamide can be carried out batchwise or continuously in one and the same distillation column. The high-quality N-(2-chloroethyl) methanesulfonamide which has been obtained as described above is a colorless product.

When the extraction is carried out with water after the completion of the reaction, an amount of water to be charged is necessary to be minimized in respect of decreasing waste water, so the amount is generally 5 to 50% by weight, preferably 10 to 20% by weight based on the reaction solution. Extraction temperature is generally 20° to 80° C., preferably 20° to 50° C., and although extraction time is not limited, it is generally 0.2 to 2 hours. After the extraction, an aqueous layer is separated, ethylene dichloride in an organic layer is separated and recovered by distillation, and then the separated ethylene dichloride is used in the following reaction as it is or after purification, if necessary. After recovering ethylene dichloride, aimed N-(2-chloroethyl) methanesulfonamide is obtained from the organic layer by vacuum distillation. Distillation condition is 0.1 to 10 torr of a pressure and 100° to 200° C. of a distillation temperature. Separation of ethylene dichloride and a light fraction and recovery of N-(2-chloroethyl) methanesulfonamide may be carried out in a single distillation column batchwise or continuously.

The N-(2-chloroethyl) methanesulfonamide having high purities is obtained as colorless product.

Now, this invention will be described more specifically below with reference to working examples. It should be noted, however, that this invention is not limited to or by these working examples.

EXAMPLE 1

In a reaction vessel made of glass and provided with a stirrer, a reflux condenser, a raw material charging tube, and a thermometer, 540 g of ethylene dichloride was placed and then stirred and heated up to 83° C. under normal pressure. Then, dropwise addition of 540 g of methanesulfonyl chloride thereto at a rate of 18 g per minute was started. When the amount of methanesulfonyl chloride thus added reached 54 g, the supply of 207 g of ethylene imine thereto through the charging tube at a rate of 6.9 g per minute was started. During the supply of ethylene imine and methanesulfonyl chloride, the reaction solution continued to boil at a temperature in the range of from 83° to 96° C. Ethylene dichloride which was evaporated from the reaction solution during the supply of ethylene imine and methanesulfonyl chloride was condensed in a condenser and refluxed to the reaction vessel. The total time required for the supply of ethylene imine and methanesulfonyl chloride was 33 minutes. After the supply of ethylene imine and methanesulfonyl chloride was completed, the reaction solution was stirred further at the boiling temperature for 10 minutes to complete the reaction.

From the reaction solution thus obtained, ethylene dichloride was recovered by distillation. Then, the reaction solution remaining after the separation of ethylene dichloride was subjected to vacuum distillation in a thin-film distillation vessel under a vacuum of 1 torr at a temperature of 160° C., to obtain 684 g of N-(2-chloroethyl) methanesulfonamide. This amount of the product represents 92% of the theoretical yield based on the methanesulfonyl chloride consumed in the reaction. The purity of the produced N-(2-chloroethyl) methanesulfonamide, on analysis by liquid chromatography, was found to be 99.9%. This product was colorless and transparent.

EXAMPLE 2

In a reaction vessel made of glass and provided with a stirrer, a reflux condenser, a raw material charging tube, and a thermometer, 600 g of ethylene dichloride was placed and then stirred and heated up to 83° C. under normal pressure. Then, dropwise addition of 1,145 g of methanesulfonyl chloride thereto at a rate of 6.4 g per minute was started. When the amount of methanesulfonyl chloride thus added reached 57 g, the supply of 440 g of ethylene imine thereto through the charging tube at a rate of 2.4 g per minute was started. During the supply of ethylene imine and methanesulfonyl chloride, the reaction solution continued to boil at a temperature in the range of from 83° to 97° C. Ethylene dichloride which was evaporated from the reaction solution during the supply of ethylene imine and methanesulfonyl chloride was condensed in a condenser and refluxed to the reaction vessel. The total time required for the supply of ethylene imine and methanesulfonyl chloride was 3 hours. After the supply of ethylene imine and methanesulfonyl chloride was completed, the reaction solution was stirred further at the boiling temperature for 30 minutes to complete the reaction. The reaction mixture in the flask was further stirred at this temperature for 30 minutes to complete the reaction. The resultant reaction solution was cooled to room temperature. The cooled reaction solution and 400 g of water added thereto were stirred for 30 minutes and left standing at rest for one hour. The aqueous layer formed consequently in the flask was separated and discharged. The organic layer which remained was transferred into a distillation vessel, subjected therein to vacuum distillation to expel ethylene dichloride by vaporization, and then further distilled under a vacuum degree of 3 torr at a temperature of 141° to 143° C., to obtain N-(2-chloroethyl) methanesulfonamide in a yield of 85.0% based on methanesulfonyl chloride. The purity of the produced N-(2-chloroethyl) methanesulfonamide, on analysis by gas chromatography, was found to be 99.9%. This product was devoid of color.

What is claimed is:

1. A method for the production of N-(2-chloroethyl) methanesulfonamide of high purity, which method comprises causing methanesulfonyl chloride to react with ethyleneimine in the presence of ethylene dichloride, at a reaction temperature commenced and completed in the range 50° to 150° C., and then distilling the resultant reaction mixture thereby separating therefrom N-(2-chloroethyl) methanesulfonamide.

2. A method according to claim 1, wherein the amount of ethylene dichloride is in the range of from 50 to 1,000 parts by weight, based on 100 parts by weight of methanesulfonyl chloride.

3. A method according to claim 2, wherein the amount of methanesulfonyl chloride is in the range of from 0.9 to 1.1 mols per mol of ethylene imine.

4. A method according to claim 1, wherein the reaction is carried out by supplying ethylene imine and methanesulfonyl chloride to a reaction vessel at the same time.

5. A method according to claim 1, wherein the reaction is carried out by supplying ethylene imine into a reaction solution.

6. A method according to claim 1, wherein the reaction is carried out at a boiling temperature of the reaction solution.

7. A method for the production of N-(2-chloroethyl) methanesulfonamide of high purity, which method comprises causing methanesulfonyl chloride to react with ethylene imine in the presence of ethylene dichloride, at a reaction temperature commenced and completed in the range 50° to 150° C., subjecting the resultant reaction mixture to extraction from water, separating the aqueous layer consequently formed, and subjecting the organic layer resulting from said extraction to distillation thereby separating N-(2-chloroethyl) methanesulfonamide.

8. A method according to claim 7, wherein the amount of ethylene dichloride is in the range of from 50 to 1,000 parts by weight, based on 100 parts by weight of methanesulfonyl chloride.

9. A method according to claim 8, wherein the amount of methanesulfonyl chloride is in the range of from 0.9 to 1.1 mols per mol of ethylene imine.

10. A method according to claim 7, wherein the reaction is carried out by supplying ethylene imine and methanesulfonyl chloride to a reaction vessel at the same time.

11. A method according to claim 7, wherein the reaction is carried out by supplying ethylene imine into a reaction solution.

12. A method according to claim 1, wherein the reaction is carried out at a boiling temperature of the reaction solution.

13. A method according to claim 7, wherein the amount of water is in the range of from 5 to 50% by weight, based on the amount of said organic layer.

14. A method according to claim 7, wherein the extraction temperature is in the range of from 20° to 80° C.

* * * * *